US012749572B2

(12) United States Patent
Okamoto

(10) Patent No.: US 12,749,572 B2
(45) Date of Patent: Sep. 29, 2026

(54) ELECTROCARDIOGRAPHIC SIGNAL ANALYSIS SYSTEM

(71) Applicant: Toray Industries, Inc., Tokyo (JP)

(72) Inventor: Riku Okamoto, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 18/847,809

(22) PCT Filed: Feb. 17, 2023

(86) PCT No.: PCT/JP2023/005851
§ 371 (c)(1),
(2) Date: Sep. 17, 2024

(87) PCT Pub. No.: WO2023/188982
PCT Pub. Date: Oct. 5, 2023

(65) Prior Publication Data

US 2025/0210187 A1 Jun. 26, 2025

(30) Foreign Application Priority Data

Mar. 29, 2022 (JP) ................................ 2022-053215

(51) Int. Cl.
*G16H 40/63* (2018.01)
*A61B 5/308* (2021.01)
*A61B 5/352* (2021.01)

(52) U.S. Cl.
CPC ............. *G16H 40/63* (2018.01); *A61B 5/308* (2021.01); *A61B 5/352* (2021.01)

(58) Field of Classification Search
CPC ........ G16H 40/63; A61B 5/308; A61B 5/352; A61B 5/346; A61B 5/349; A61B 5/366; A61B 5/7221; A61B 5/7225
See application file for complete search history.

(56) References Cited

U.S. PATENT DOCUMENTS

| | | | | |
|---|---|---|---|---|
| 10,918,302 B2 * | 2/2021 | Matsuura | ............... | A61B 5/352 |
| 2004/0042581 A1 * | 3/2004 | Okerlund | ............... | A61B 5/352<br>378/4 |
| 2021/0106246 A1 * | 4/2021 | Stickney | ............... | A61B 5/273 |

FOREIGN PATENT DOCUMENTS

| | | |
|---|---|---|
| CN | 104161510 A | 11/2014 |
| CN | 111513706 A | 8/2020 |

(Continued)

OTHER PUBLICATIONS

International Search Report (PCT/ISA/210) with translation and Written Opinion (PCT/ISA/237) mailed Apr. 18, 2023, by the Japan Patent Office as the International Searching Authority for International Application No. PCT/JP2023/005851. (8 pages).

(Continued)

*Primary Examiner* — Chinyere Mpamugo
(74) *Attorney, Agent, or Firm* — Buchanan Ingersoll & Rooney PC

(57) ABSTRACT

An electrocardiographic signal analysis system includes: an input unit configured to receive input of electrocardiographic information; a unit waveform data extracting unit configured to perform segmentation and extract unit waveform data based on a peak of an R wave or an S wave from waveform data included in the electrocardiographic information; a loss detection unit configured to detect a loss portion of a peak of an R wave or an S wave in the unit waveform data using an extreme value immediately before or immediately after the peak or using a point of inflection immediately before or immediately after the peak; and a data interpolation unit configured to set a wave height or a cycle of a waveform after interpolation based on a peak position of an R wave or an S wave of a waveform obtained by interpolating the loss portion.

9 Claims, 10 Drawing Sheets

(56) References Cited

FOREIGN PATENT DOCUMENTS

| | | |
|---|---|---|
| JP | 2019051011 A | 4/2019 |
| WO | 2017135116 A1 | 8/2017 |

OTHER PUBLICATIONS

Castiglioni et al., "Interpolation technique for extracting features from ECG signals sampled at low sampling rates", Computers in Cardiology 2003, (Sep. 21, 2003), vol. 30, pp. 481-484.
Zhu et al., "A Flattest Constrained Envelope Approach for Empirical Mode Decomposition", PLOS ONE, (Apr. 23, 2013), vol. 8, No. 4, e61739, pp. 1-12.
Extended European Search Report issue Jan. 28, 2026, by the European Patent Office in corresponding European Patent Application No. 23779012.6-1113. (5 pages).

* cited by examiner (a)

(b)

ELECTROCARDIOGRAPHIC SIGNAL ANALYSIS SYSTEM

CROSS REFERENCE TO RELATED APPLICATIONS

This application is the U.S. National Phase of PCT/JP2023/005851, filed Feb. 17, 2023 which claims priority to Japanese Patent Application No. 2022-053215, filed Mar. 29, 2022, the disclosures of these applications being incorporated herein by reference in their entireties for all purposes.

FIELD OF THE INVENTION

The present invention relates to an electrocardiographic signal analysis system that estimates a measurement state of electrocardiographic signals based on, for example, electrocardiographic signals (hereinafter, electrocardiographic information).

BACKGROUND OF THE INVENTION

The heart functions as a pump that repeats contraction and expansion to send blood throughout the body. This activity is regulated by weak electrical stimulation in myocardial cells, and occurrence of abnormality in this electrical stimulation also causes abnormality in the heart activity. This abnormality in the activity of the heart is called arrhythmia. There are various types of arrhythmias, and examples thereof include highly fatal ventricular fibrillation that causes cardiac arrest, ventricular tachycardia, and atrial fibrillation that causes cerebral infarction. Therefore, it is essential to determine the arrhythmia, which is determined using electrocardiographic information acquired from a determination target by an electrocardiographic signal measuring instrument.

Since waveform data indicated by the electrocardiographic information can be divided at intervals (hereinafter, cycles) from previous and subsequent waveforms or the height (hereinafter, the wave height) of the waveform, systems that automatically determine the arrhythmia by calculating the cycle or the wave height from electrocardiographic information are widely used. However, in electrocardiographic information acquired by an electrocardiographic signal measuring instrument, the actual cycle or wave height may not be calculated due to an influence of a measurement failure of the measuring instrument or external disturbance.

For this problem, for example, Patent Literature 1 describes a method of detecting an abnormal period or wave height and interpolating for the portion with the abnormality. Specifically, in Patent Literature 1, in a case where a cycle or a wave height calculated from electrocardiographic information is out of a normal range, target data is determined as abnormal, and interpolation is performed based on previous and subsequent normal cycles or wave heights.

PATENT LITERATURE

Patent Literature 1: WO 2017/135116 A

SUMMARY OF THE INVENTION

Meanwhile, in measured electrocardiographic information, a loss may occur at a waveform peak. A peak loss refers to the occurrence of a recess or the like in a peak of an R wave or an S wave of the obtained waveform due to a measurement failure of the measuring instrument or external disturbance. The cycle or the wave height calculated from an electrocardiographic waveform in which a peak loss is occurring is different from an actual cycle or wave height; however, the gap is small. In the method of Patent Literature 1 or the like, the peak loss is not considered, and it is difficult to determine a peak loss as an abnormality. Therefore, it is not possible to calculate the actual cycle and wave height of an electrocardiographic waveform in which a peak loss occurs only by applying Patent Literature 1, and thus erroneous determination of arrhythmia may be caused.

An object of the present invention is to provide an electrocardiographic signal analysis system capable of optimizing the waveform in a case where a peak loss occurs in an electrocardiographic waveform by solving the above problems of the prior art.

An electrocardiographic signal analysis system of the present invention that achieves the above object has the following configuration.

(1) An electrocardiographic signal analysis system that acquires electrocardiographic information and performs processing, the electrocardiographic signal analysis system including: an input unit configured to receive input of the electrocardiographic information; a unit waveform data extracting unit configured to perform segmentation and extract unit waveform data based on a peak of an R wave or an S wave from waveform data included in the electrocardiographic information; a loss detection unit configured to detect a loss portion of a peak of an R wave or an S wave in the unit waveform data using an extreme value immediately before or immediately after the peak or using a point of inflection immediately before or immediately after the peak; and a data interpolation unit configured to set a wave height or a cycle of a waveform after interpolation based on a peak position of an R wave or an S wave of a waveform obtained by interpolating the loss portion.

(2) The electrocardiographic signal analysis system according to (1), wherein concerning the unit waveform data, the loss detection unit is configured to determine whether or not a minimum point immediately before or immediately after the peak of the R wave exceeds a reference or whether or not a maximum point immediately before or immediately after the peak of the S wave is below a reference to detect the peak loss.

(3) The electrocardiographic signal analysis system according to (1), wherein concerning the unit waveform data, the loss detection unit is configured to determine whether or not a maximum point immediately before or immediately after the peak of the R wave exceeds a reference or whether or not a minimum point immediately before or immediately after the peak of the S wave is below a reference to detect the peak loss.

(4) The electrocardiographic signal analysis system according to (1), wherein concerning the unit waveform data, the loss detection unit is configured to determine whether or not the point of inflection immediately before or immediately after the peak of the R wave exceeds a reference or whether or not the point of inflection immediately before or immediately after the peak of the S wave is below a reference to detect the peak loss.

(5) The electrocardiographic signal analysis system according to any one of (1) to (4), further including: a filter processing unit that applies a filter to the electrocardiographic information acquired by the input unit to pass the characteristic frequency and outputs filtered electrocardiographic information, wherein the unit waveform data extracting unit is configured to extract the unit waveform data based on the filtered electrocardiographic information.

(6) The electrocardiographic signal analysis system according to any one of (1) to (4), further including: a filter processing unit that applies a filter to the electrocardiographic information acquired by the input unit to retain the frequency components of both or either the R wave and the S wave, and outputs filtered electrocardiographic information, wherein the unit waveform data extracting unit is configured to extract the unit waveform data based on the filtered electrocardiographic information, and when any one of an average value, a maximum value, or a minimum value of wave heights in the unit waveform data is used as a reference, the wave height set by the data interpolation unit is a relative amount concerning the reference.

(7) The electrocardiographic signal analysis system according to any one of (1) to (4), wherein the data interpolation unit is configured to generate interpolation data in which the peak loss portion is interpolated.

Advantageous Effects of Invention

According to the present invention, the waveform can be optimized in a case where a peak loss occurs in an electrocardiographic waveform.

DETAILED DESCRIPTION OF EMBODIMENTS OF THE INVENTION

Hereinafter, embodiments of an electrocardiographic signal analysis system according to the present invention will be described in detail with reference to the drawings. Note that the present invention is not limited by the embodiments. Moreover, individual embodiments of the present invention are not independent and can be combined for implementation as appropriate.

First Embodiment

Figure 1:
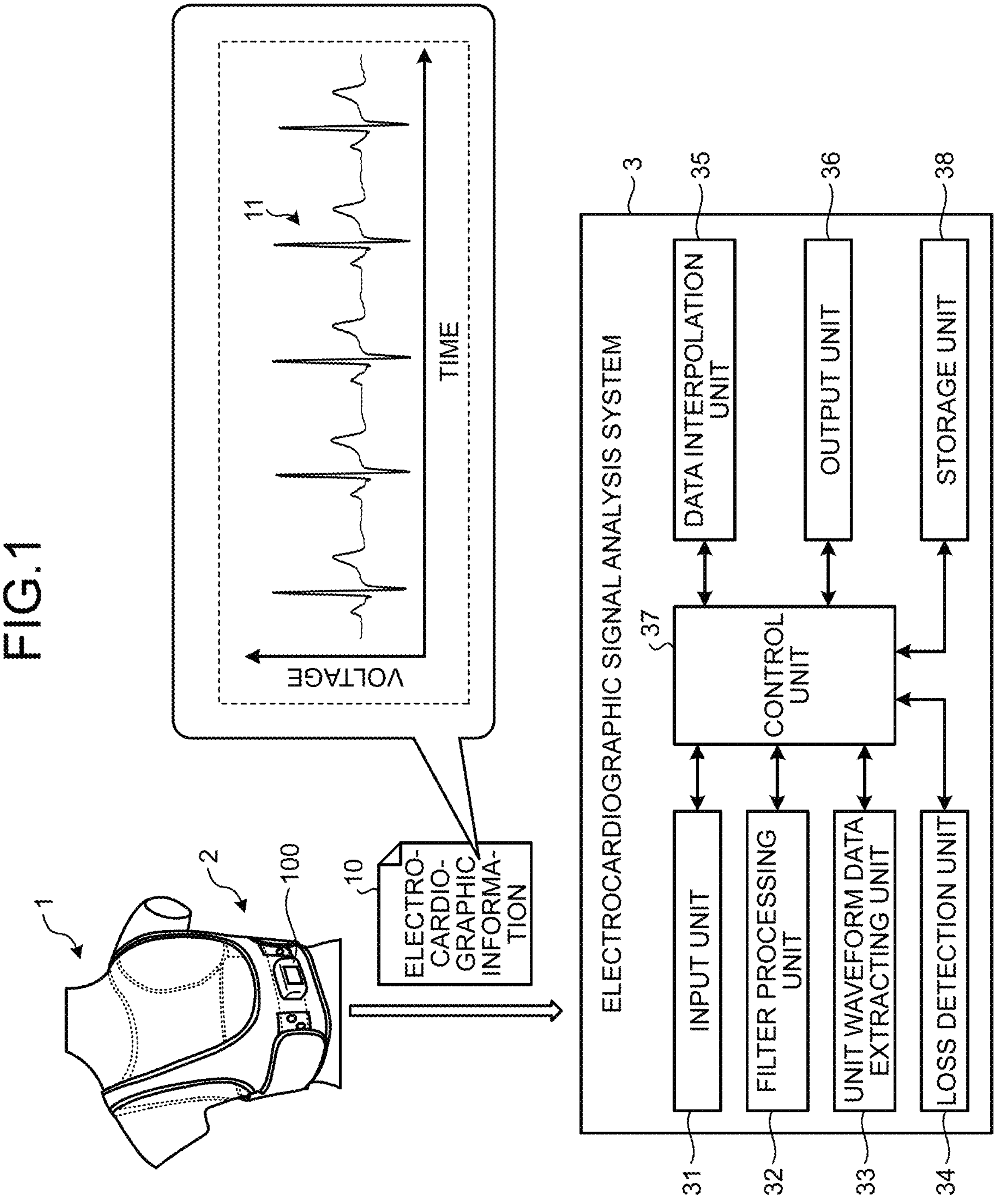
FIG. 1 is a diagram illustrating a configuration example of an electrocardiographic signal analysis system according to a first embodiment.

FIG. 1 is a diagram illustrating a configuration example of an electrocardiographic signal analysis system according to a first embodiment of the present invention. According to FIG. 1, electrocardiographic information 10 to be analyzed is acquired from a subject 1 via an electrocardiographic signal measuring instrument 2. The electrocardiographic information herein indicates a minute amount of current generated with contraction and expansion of the heart. The subject 1 is not particularly limited such as a human or an animal.

Examples of the electrocardiographic signal measuring instrument 2 include a wearable electrocardiograph. Specifically, the electrocardiographic signal measuring instrument 2 includes a plurality of electrodes provided to the main body of an outfit worn by the subject 1 and an electrocardiographic signally connected to each of the electrodes.

The electrocardiograph 100 an example of an electrocardiographic signal measuring instrument that measures an electrocardiographic signal of a subject. The electrocardiograph 100 has a function of continuously measuring an electrocardiographic signal (the electrocardiographic information 10) of a subject, a function of storing the obtained electrocardiographic information 10, and a function of transferring data by communication with an electrocardiographic signal analysis system 3. Note that the electrocardiograph 100 transfer data including the electrocardiographic information 10 to a server device, and the server device may transfer the electrocardiographic information 10 to the electrocardiographic signal analysis system 3. Hereinafter, description will be given on the premise that the subject 1 refers to a person wearing the electrocardiographic signal measuring instrument 2.

The electrocardiographic information 10 acquired from the subject 1 includes information of the subject 1, acquisition date and time, a location, and a measurement result. The measurement result is waveform data 11 obtained by plotting on the horizontal axis as time and the vertical axis as voltage (see FIG. 1).

Figure 2:
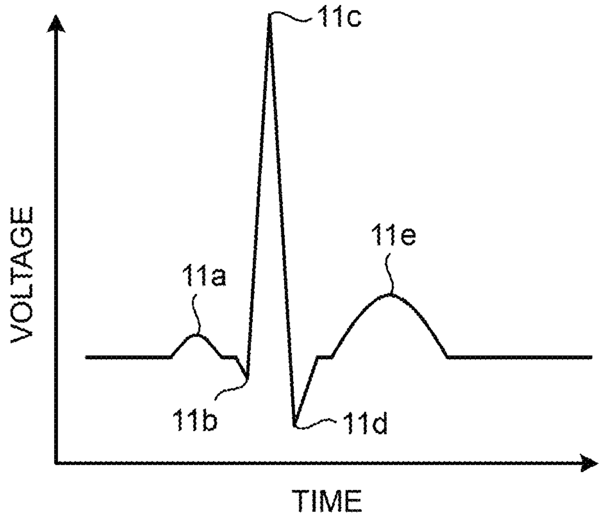
FIG. 2 is a diagram illustrating a detailed example of electrocardiographic information used for analysis.

FIG. 2 is a diagram illustrating a detailed example of the electrocardiographic information 10 used for analysis. The waveform data 11 may include components referred to as a P wave 11*a*, a Q wave 11*b*, an R wave 11*c*, an S wave 11*d*, and a T wave 11*e*, and these shapes are used as determination criteria for arrhythmia. Note that the shape of the waveform data 11 included in the electrocardiographic information 10 may change depending on the subject or the position of the electrocardiogram the subject.

Returning to FIG. 1, the electrocardiographic signal analysis system 3 according to the present invention includes an input unit 31, a filter processing unit 32, a unit waveform data extracting unit 33, a loss detection unit 34, a data interpolation unit 35, an output unit 36, a control unit 37, and a storage unit 38.

The input unit 31 receives input of the electrocardiographic information 10 output from the electrocardiographic signal measuring instrument 2. The input unit 31 includes a connector electrically connected to the electrocardiographic signal measuring instrument 2, a communication device including a communication means with the electrocardiographic signal measuring instrument 2, or an input port of a medium storing data and may further include a user interface such as a keyboard, a mouse, or a microphone.

The filter processing unit 32 performs filter processing on the waveform data 11 of the electrocardiographic information 10.

The unit waveform data extracting unit 33 extracts unit waveform data 13 from electrocardiographic information (waveform data) 12 having been subjected to filter processing.

The loss detection unit 34 detects a loss of a peak of an R wave or an S wave in the waveform indicated by the unit waveform data 13.

The data interpolation unit 35 interpolates a peak loss portion detected by the loss detection unit 34.

The output unit 36 includes an output device such as a display device or a printing device and outputs various types of information under the control by the control unit 37. The output unit 36 has, for example, a sound output function of a display including liquid crystal, organic electro luminescence (EL), or the like, a speaker, or the like.

The control unit 37 integrally controls the operation of the electrocardiographic signal analysis system 3. In addition, the control unit 37 causes the display to display the electrocardiographic information 10, information of normality and arrhythmia determined based on the electrocardiographic information 10, the interpolation result by the data interpolation unit 35, and the like or outputs the information to the outside.

The storage unit 38 stores various programs for operating the electrocardiographic signal analysis system 3 or various types of data including data generated by the units. The various programs also include a determination program executed using a learning model. The storage unit 38 includes a read only memory (ROM) in which various programs and the like are installed in advance, a random access memory (RAM) that stores calculation parameters, data, and the like of each processing, a hard disk drive (HDD), a solid state drive (SSD), and the like.

The various programs can be recorded on a computer-readable recording medium such as an HDD, a flash memory, a CD-ROM, a DVD-ROM, or Blu-ray® and widely distributed. Furthermore, the input unit 31 can acquire the various programs via a communication network. The communication network mentioned here is configured using, for example, an existing public line network, a local area network (LAN), a wide area network (WAN), or the like and may be either wired or wireless.

The electrocardiographic signal analysis system 3 having the above functional configuration is a computer configured using one or a plurality of pieces of hardware such as a central processing unit (CPU), a graphics processing unit (GPU), an application specific integrated circuit (ASIC), and a field programmable gate array (FPGA).

Figure 3:
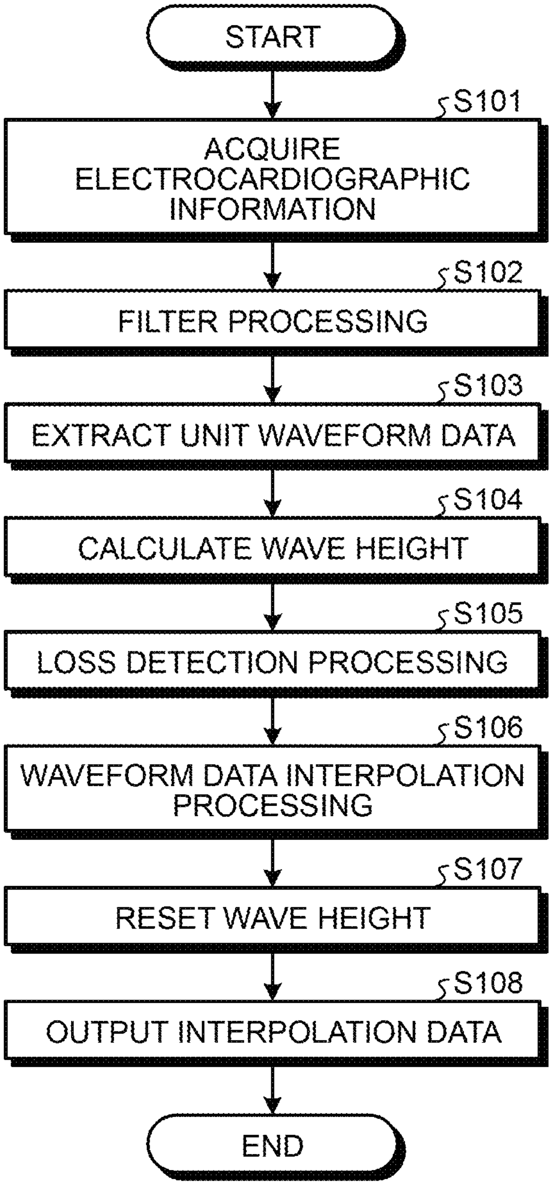
FIG. 3 is a flowchart illustrating noise determination processing according to the first embodiment.

Next, noise determination processing based on the electrocardiographic information 10 obtained from the subject 1 will be described. FIG. 3 is a flowchart illustrating the noise determination processing according to the first embodiment. In the noise determination processing, first, the input unit 31 acquires the electrocardiographic information 10 obtained from the subject 1 via the electrocardiographic signal measuring instrument 2 (step S101).

The filter processing unit 32 performs filter processing on the waveform data 11 acquired in step S101 (step S102). For example, the filter processing unit 32 reduces the difference between the normal sinus rhythm and arrhythmia by allowing only the features of the electrocardiographic signal to pass from the waveform data 11 indicating the relationship between time and intensity (here, voltage), thereby making a difference from the noise obvious. Specifically, the filter processing unit 32 applies a frequency filter to the electrocardiographic information 10 input by the input unit 31 to generate the filtered electrocardiographic information (waveform data) 12 in which only characteristic frequencies of the normal sinus rhythm and the arrhythmia are allowed to pass. For example, the filter processing unit 32 applies a filter that leaves frequency components of both or one of an R wave and an S wave to output the filtered electrocardiographic information (waveform data) 12. As a specific pass band of the frequency filter, 5 to 50 Hz or the like is set; however, it is not limited thereto. The frequency filter is designed using a general infinite impulse response (IIR) filter or a finite impulse response (FIR) filter.

Figure 4A:
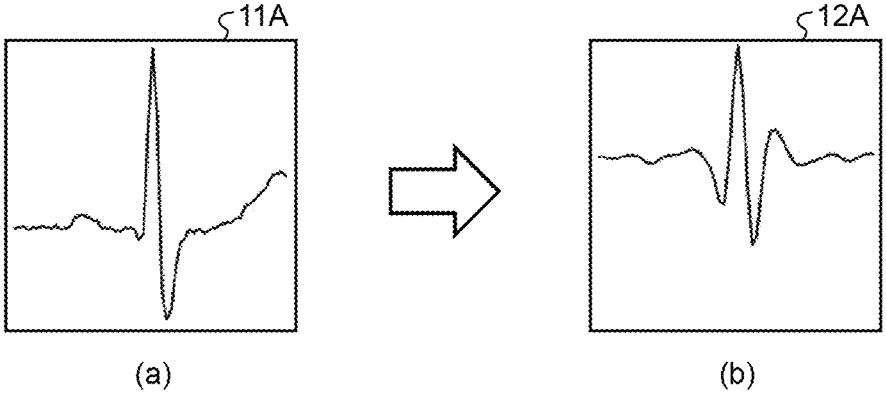
FIG. 4A is a diagram (part 1) for describing a processing example of a filter processing unit.
Figure 4B:
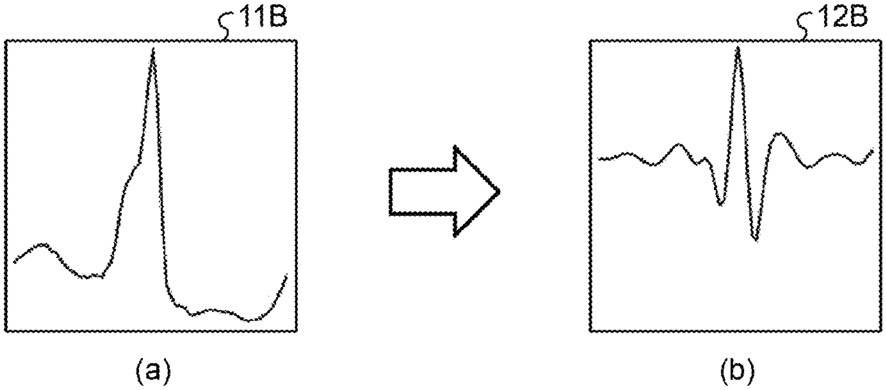
FIG. 4B is a diagram (part 2) for explaining a processing example of the filter processing unit.
Figure 4C:
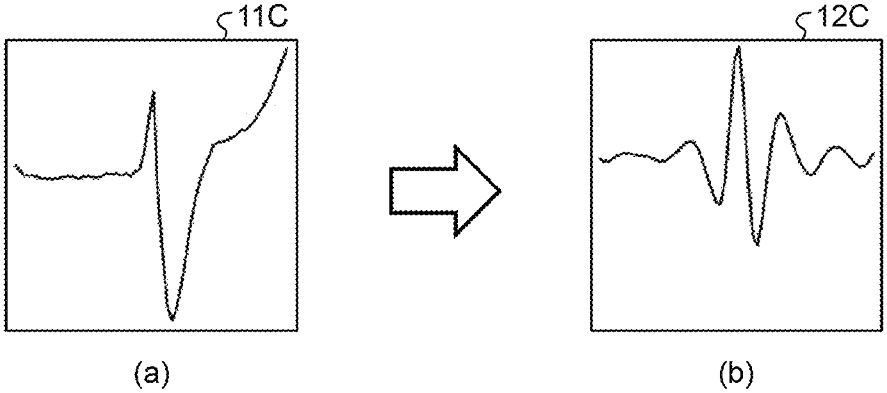
FIG. 4C is a diagram (part 3) for describing a processing example of the filter processing unit.

FIGS. 4A to 4C are diagrams for describing a processing example of the filter processing unit according to the first embodiment. Executing filter processing on waveform data 11A to 11C illustrated in (a) of FIGS. 4A to 4C results in generation of filtered electrocardiographic information (waveform data) 12A to 12C (see (b) of FIGS. 4A to 4C). The generated filtered electrocardiographic information (waveform data) 12 is registered in the storage unit 38.

Figure 5:
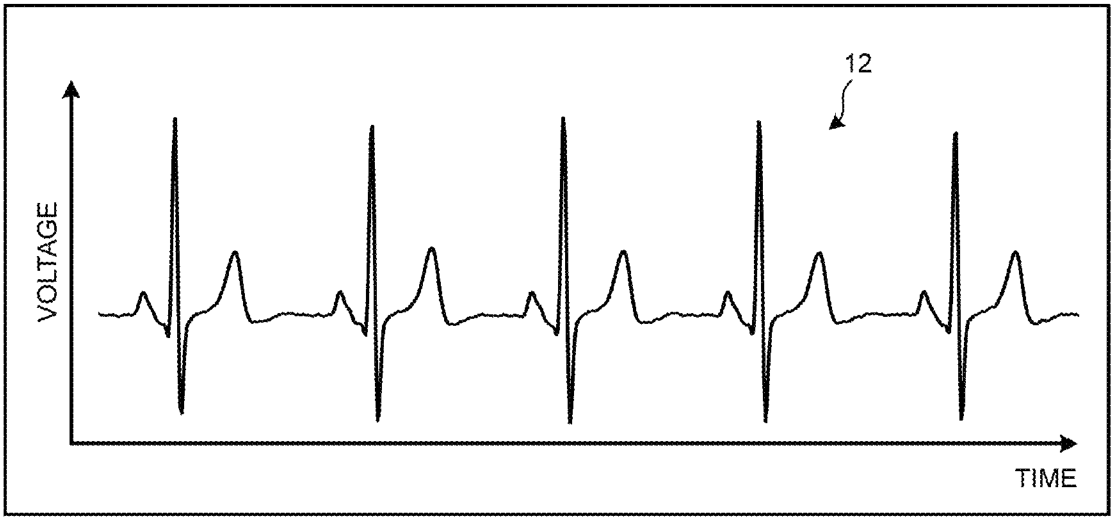
FIG. 5 is a diagram (part 1) illustrating a processing example of a unit waveform data extracting unit.
Figure 5:
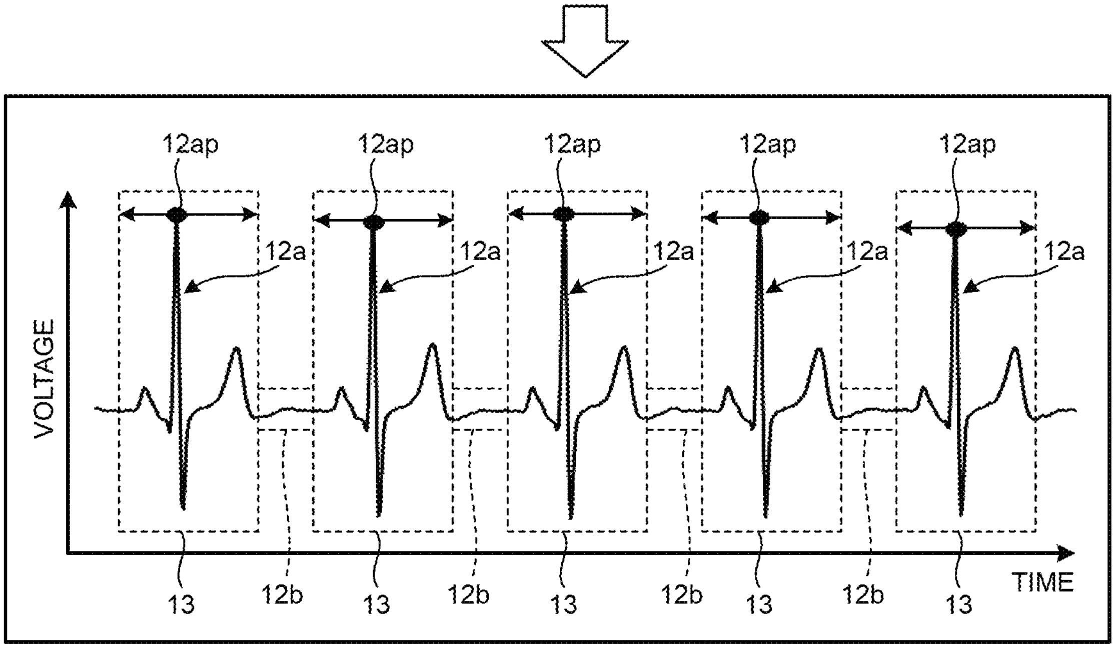

After the filter processing, the unit waveform data extracting unit 33 generates the unit waveform data 13 obtained by partial extraction from the waveform data 12 (step S103). FIG. 5 is a diagram illustrating a processing example of the unit waveform data extracting unit. The unit waveform data extracting unit 33 generates the unit waveform data 13 in which each designated unit is extracted from the waveform data 12 illustrated in (a) of FIG. 5 (see (b) of FIG. 5) and stores the unit waveform data 13 in the storage unit 38. It is conceivable that extraction of the unit waveform data 13 is performed using, for example, a designated period based on time axis information as a unit or using an R wave 12*a* as an extraction reference position, and then define a designated number of waveforms as a unit; however, it is not limited thereto. In the example illustrated in FIG. 5, a peak position 12*ap* of the R wave 12*a* is detected, and a designated number of seconds before and after the peak position 12*ap* of the R wave 12*a* is set as one unit, whereby the unit waveform data 13 represents a single waveform based on the waveform data 12.

Incidentally, in the waveform data 12 (or the waveform data 11), intervals between the pieces of the unit waveform data 13 are not constant due to heart rate fluctuation. However, with segmentation into each unit waveform, an effect of improving the accuracy of loss detection by the loss detection unit 34 or interpolation by the data interpolation unit 35 and an effect of improving the accuracy of arrhythmia determination can be expected. In addition, since a section having no useful information for determination, such as out-of-unit waveform data 12*b* in (b) of FIG. 5, is excluded, the processing amount can be suppressed.

In addition, in the example illustrated in FIG. 5, in order to perform segmentation into unit waveforms, the designated number of seconds before and after (for example, 0.4 seconds) the peak position 12*ap* of the R wave 12*a* detected from the maximum value in a certain section is set as one unit waveform; however, it is not limited thereto. In a case where the waveform data does not have the R wave 11*c* and the peak position 12*ap* of the R wave 12*a* cannot be detected, the input unit 31 obtains the maximum value of the waveform data 12, uses the maximum value as the reference point, and defines a designated number of seconds before and after this maximum value as one unit.

Then, the unit waveform data extracting unit 33 calculates the wave height for the unit waveform data 13 (step S104). Hereinafter, an example of calculating only the wave height will be described; however, only the cycle may be calculated, or the wave height and the cycle may be calculated. The wave height indicates the height of a waveform, and the cycle indicates the interval between pieces of unit waveform data.

Figure 6:
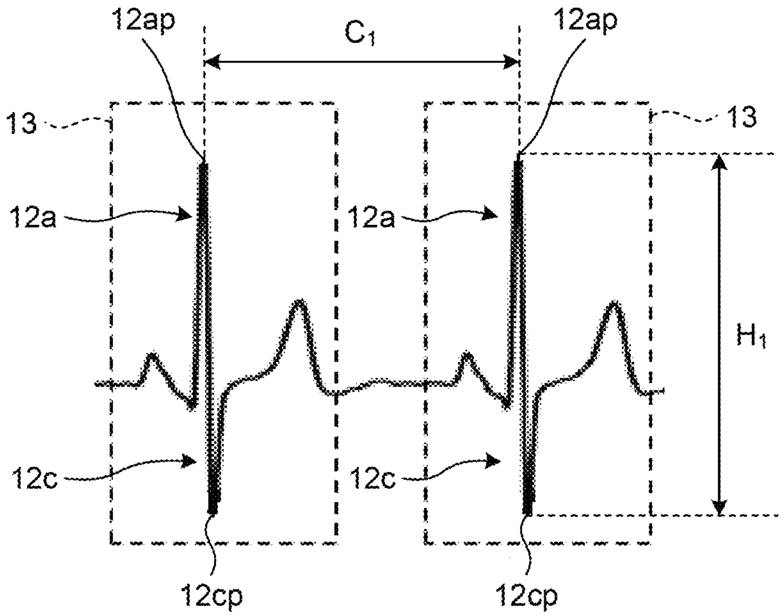
FIG. 6 is a diagram (part 2) illustrating a processing example of the unit waveform data extracting unit.

FIG. 6 is a diagram illustrating a processing example of the unit waveform data extracting unit. The unit waveform data extracting unit 33 calculates a distance $H_1$ between a peak position 12*ap* of the R wave 12*a* of the unit waveform data 13 and a peak position 12*cp* of the S wave 12*c* regarding the wave height. When calculating the cycle, the unit waveform data extracting unit 33 calculates a distance $C_1$ between peak positions 12*ap* of R waves 12*a* of the unit waveform data 13 temporally adjacent to each other.

The loss detection unit 34 detects a waveform loss in the unit waveform data 13 (step S105). The peak loss referred to herein means that a loss occurs at a peak of an R wave or an S wave of an obtained waveform due to a measurement failure of the electrocardiographic signal measuring instrument 2 or an influence of external disturbance.

Figure 7:
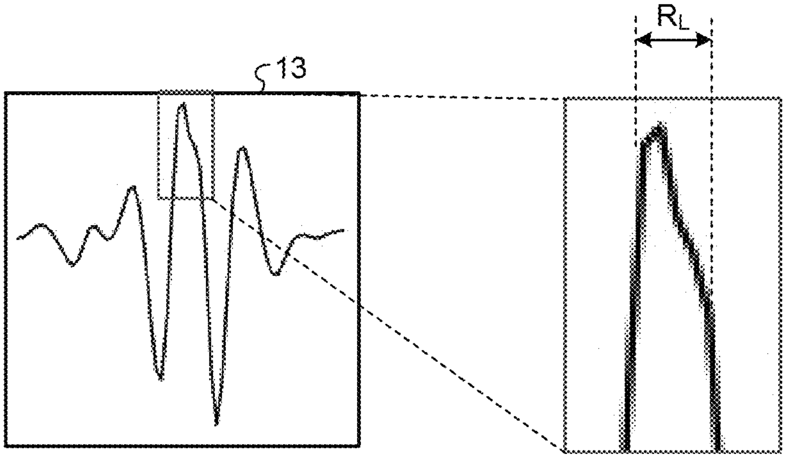
FIG. 7 is a diagram for describing an overview of processing of a loss detection unit.

FIG. 7 is a diagram for describing an overview of processing by the loss detection unit. The loss detection unit 34 detects a loss portion Ry of the waveform (R wave in FIG. 7) of the unit waveform data 13.

Specifically, as a method for detecting a peak loss, for example, an extreme value immediately before or after an R wave or S wave is used, and the extreme value is compared with a preset reference to detect a peak loss. Specifically, for example, a peak loss is detected by determining whether or not the potential of the minimum point immediately before or after an R wave peak exceeds the reference, or a peak loss is detected by determining whether or not the potential of the maximum point immediately before or after an R wave peak exceeds the reference. Similarly, for an S wave as well, a peak loss is detected by determining whether or not the potential of the maximum point immediately before or after an S wave peak is below the reference, or a peak loss is detected by determining whether or not the potential of the minimum point immediately before or after an S wave peak is below the reference. In this manner, a spike-like peak loss can be detected.

As a method of setting the reference for detecting a peak loss, for example, it is assumed that a baseline (zero point) of the electrocardiographic information 10 is used or that a value of 50% of the potential from the baseline to an R wave peak is used; however, an actual method is not specified, and it is merely preferable to appropriately adjust the reference by referring to the value obtained by the above method, for example.

Alternatively, as another method for detecting a peak loss, a point of inflection immediately before or after an R wave or S wave peak is used, and the potential at the point of inflection is compared with a preset reference to detect a peak loss. Specifically, for example, a peak loss is detected by determining whether or not the potential of the point of inflection immediately before or after an R wave peak exceeds the reference, or a peak loss is detected by determining whether or not the potential of the point of inflection immediately before or after an S wave peak is less than the reference. In this manner, a peak loss portion due to distortion can be detected.

Note that the reference of each extreme value or the point of inflection is set based on, for example, extreme values and points of inflection of each of waveforms in which no peak loss is occurring and waveforms in which a peak loss is occurring.

After a loss is detected, the data interpolation unit 35 interpolates data for the detected peak loss portion (step S106). As a method for interpolating the peak loss portion, a known method such as general spline interpolation can be adopted. Note that the data interpolation unit 35 also interpolates original waveform data (for example, the waveform data 11 or 12).

Figure 8A:
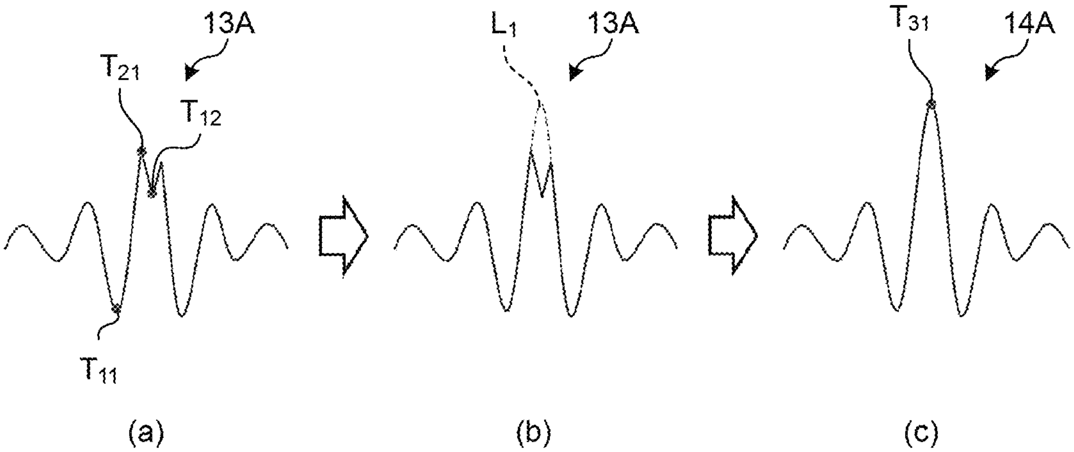
FIG. 8A is a diagram (part 1) illustrating exemplary processing of the loss detection unit and a data interpolation unit.
Figure 8B:
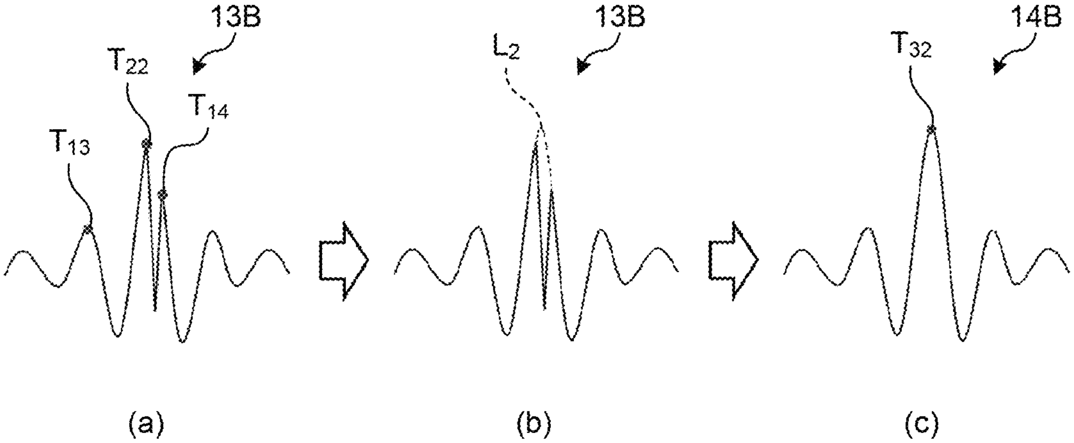
FIG. 8B is a diagram (part 2) illustrating exemplary processing of the loss detection unit and the data interpolation unit.
Figure 8C:
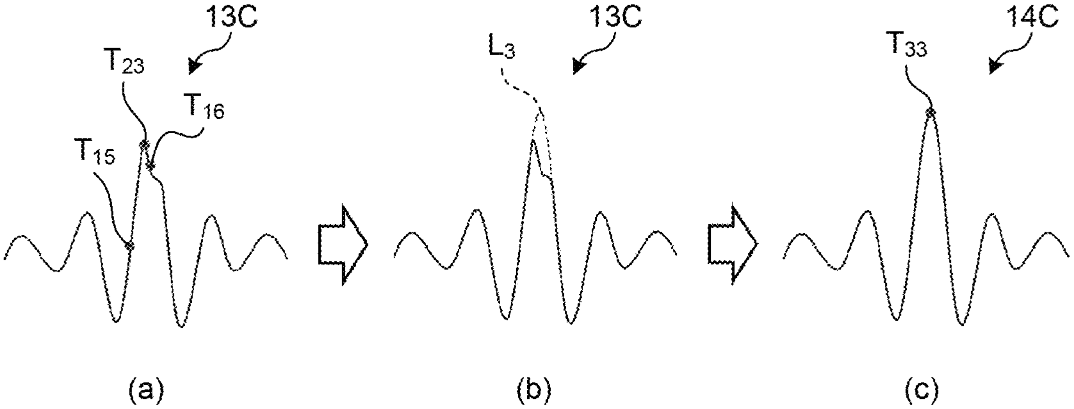
FIG. 8C is a diagram (part 3) illustrating exemplary processing of the loss detection unit and the data interpolation unit.

FIGS. 8A to 8C are diagrams for describing processing examples of the loss detection unit and the data interpolation unit according to the first embodiment. In FIGS. 8A to 8C, a waveform assumed in a case where there is no defect is indicated by a broken line. The loss portion is detected from the unit waveform data 13 by the peak loss detection described above.

Note that, in a case where no peak loss is detected, the processing for the unit waveform data 13 is ended.

[Case of Using Minimum Point Immediately Before or Immediately after Peak]

The loss detection unit 34 detects, for example, a minimum point $T_{11}$ immediately before a peak of an R wave or a minimum point $T_{12}$ immediately after the peak of the R wave for unit waveform data 13A and determines whether or not the potential of the minimum point exceeds a reference to detect a peak loss (see (a) of FIG. 8A). Then, the data interpolation unit 35 interpolates an interpolation waveform $L_1$ for the peak loss portion (see (b) of FIG. 8A) and generates interpolation data 14A (see (c) of FIG. 8A). As a result, the peak position of the R wave changes from a peak position $T_{21}$ to a peak position $T_{31}$.

[Case of Using Maximum Point of Displacement Immediately Before or Immediately after Peak]

The loss detection unit 34 detects, for example, a maximum point $T_{13}$ immediately before a peak of an R wave or a maximum point $T_{14}$ immediately after the peak of the R wave for unit waveform data 13B and determines whether or not the potential of the maximum point exceeds a reference to detect a peak loss (see (a) of FIG. 8B). Then, the data interpolation unit 35 interpolates an interpolation waveform $L_2$ for the peak loss portion (see (b) of FIG. 8B) and generates interpolation data 14B (see (c) of FIG. 8B). As a result, the peak position of the R wave changes from a peak position $T_{22}$ to a peak position $T_{32}$.

[Case of Using Point of Inflection of Displacement Immediately Before or Immediately after Peak]

The loss detection unit 34 detects, for example, a point of inflection $T_{15}$ immediately before a peak of an R wave or a point of inflection $T_{16}$ immediately after the peak of the R wave for unit waveform data 13C and determines whether or not the potential of the point of inflection exceeds a reference to detect a peak loss (see (a) of FIG. 8C). Then, the data interpolation unit 35 interpolates an interpolation waveform $L_3$ for the peak loss portion (see (b) of FIG. 8C) and generates interpolation data 14C (see (c) of FIG. 8C). As a result, the peak position of the R wave changes from a peak position $T_{23}$ to a peak position $T_{33}$.

After the interpolation processing, the data interpolation unit 35 resets the wave height for interpolation data 14 (step S107). The data interpolation unit 35 resets the wave height of the interpolation data 14 (for example, the interpolation data 14A to 14C illustrated in FIGS. 8A to 8C) based on the peak of the R wave of the waveform. As a result, the wave height calculated based on the peak of the R wave of the waveform before interpolation is changed. The wave height by the resetting processing is used for convenience of determining normality or arrhythmia and is used as the actual wave height of the electrocardiographic waveform in which the peak loss has occurred. Incidentally, the same applies to a case of using the cycle.

After the interpolation processing, the control unit 37 outputs the interpolation data 14 (step S108). The output destination is, for example, the storage unit 38 or the output unit 36. As an output mode of the interpolation data 14, it is conceivable to output the electrocardiographic information 10 input to the input unit 31 as replaced electrocardiographic information obtained by replacing a corresponding portion with the interpolated interpolation data 14; however, it is not limited thereto. It is also conceivable that a wave height or a cycle set after the interpolation is output in an integrated manner with another wave height or cycle calculated by the unit waveform data extracting unit 33; however, it is not limited thereto.

Note that it is conceivable that the above-described processing is executed each time at timing at which new electrocardiographic information is input or is executed each time at timing at which a certain amount of electrocardiographic information is accumulated; however, it is not limited thereto.

In the first embodiment described above, the peak loss of the waveform is detected based on the unit waveform data 13, and the detected peak loss is interpolated to reset the wave height of the unit waveform data 13. According to the first embodiment, in a case where the determination of the arrhythmia is applied using the reset cycle or wave height, it is possible to suppress erroneous determination due to the influence of a peak loss, and as a result, it is possible to determine normality or arrhythmia from the electrocardiographic information 10 with high accuracy.

Note that, in the first embodiment, an example in which the data interpolation unit 35 generates interpolated waveform data (the interpolation data 14) has been described. However, in order to determine normality or arrhythmia from the electrocardiographic information 10, it is not always necessary to generate the interpolation data 14, and it is sufficient to use a reset wave height. Therefore, the interpolation data 14 may not be generated. In addition, it is sufficient for the wave height that information necessary for determining normality or arrhythmia be generated from the electrocardiographic information 10, and at least one of pieces of information necessary for the determination may be calculated or reset.

In the first embodiment, the example in which the unit waveform data extracting unit 33 and the data interpolation unit 35 set the wave height has been described. However, the wave height may be set in step S107 without executing the calculation processing in step S104. In this case, in a case where no peak loss is detected, in step S107, the unit waveform data extracting unit 33 (or the data interpolation unit 35) calculates the wave height based on the unit waveform data 13. In addition, in a case where a peak loss is detected, in step S107, the data interpolation unit 35 calculates the wave height based on the unit waveform data 13 obtained by the interpolation.

Second Embodiment

Figure 9:
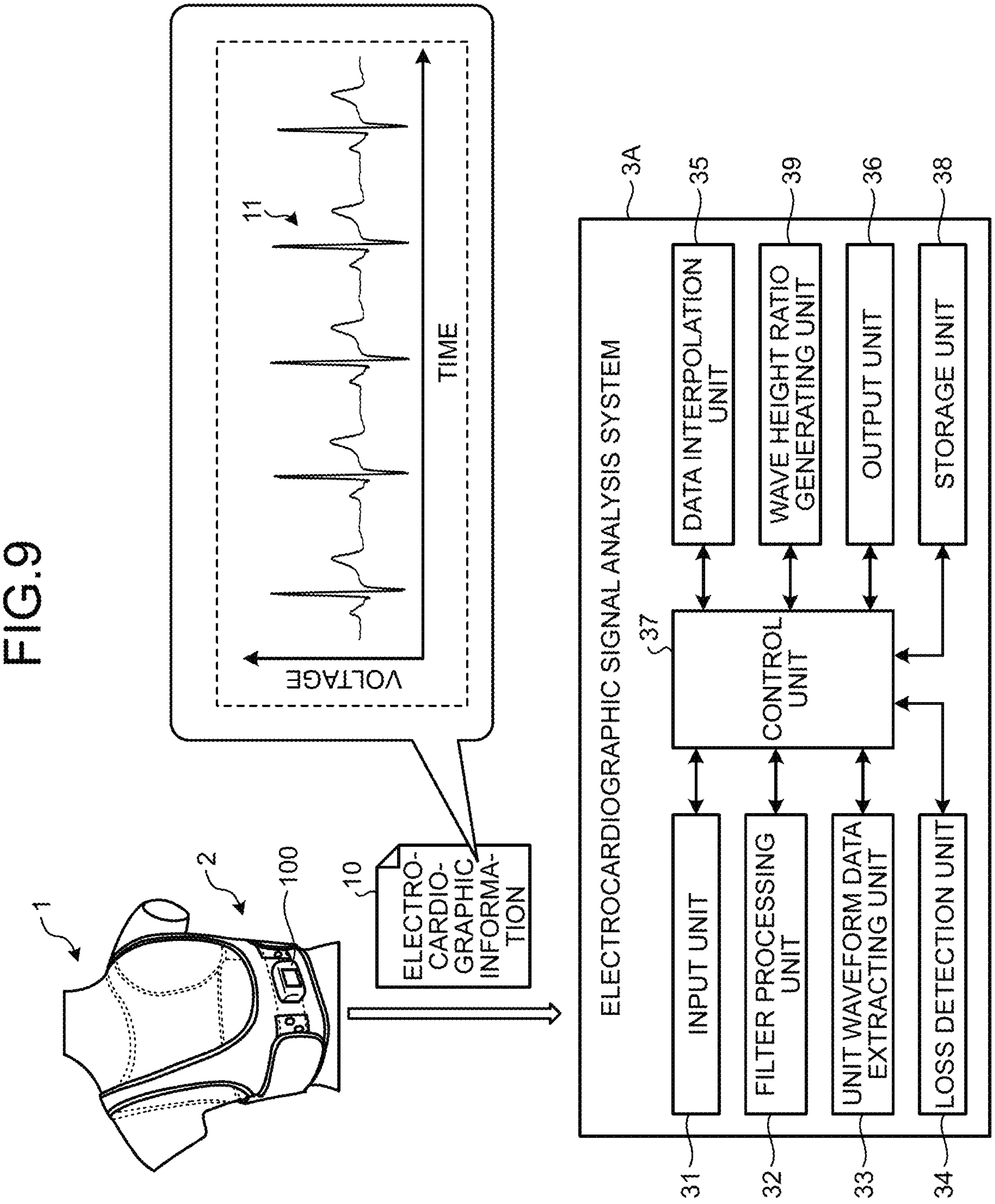
FIG. 9 is a diagram illustrating a configuration example of an electrocardiographic signal analysis system according to a second embodiment.

Next, a second embodiment of the present invention will be described. FIG. 9 is a diagram illustrating a configuration example of an electrocardiographic signal analysis system according to a second embodiment. The second embodiment includes an electrocardiographic signal analysis system 3A instead of the electrocardiographic signal analysis system 3 according to the first embodiment. In the electrocardiographic signal analysis system 3A, the same components as those of the electrocardiographic signal analysis system 3 are denoted by the same reference numerals, and description thereof will be omitted. Hereinafter, points different from those of the first embodiment will be described.

The electrocardiographic signal analysis system 3A according to the second embodiment includes an input unit 31, a filter processing unit 32, a unit waveform data extracting unit 33, a loss detection unit 34, a data interpolation unit 35, an output unit 36, a control unit 37, a storage unit 38, and a wave height ratio generating unit 39.

The wave height ratio generating unit 39 aggregates wave heights associated with respective pieces of unit waveform data 13 included in electrocardiographic information and generates, when any one of the average value, the maximum value, and the minimum value of the wave heights is used as a reference, a wave height ratio that is a relative amount concerning the reference.

Figure 10A:
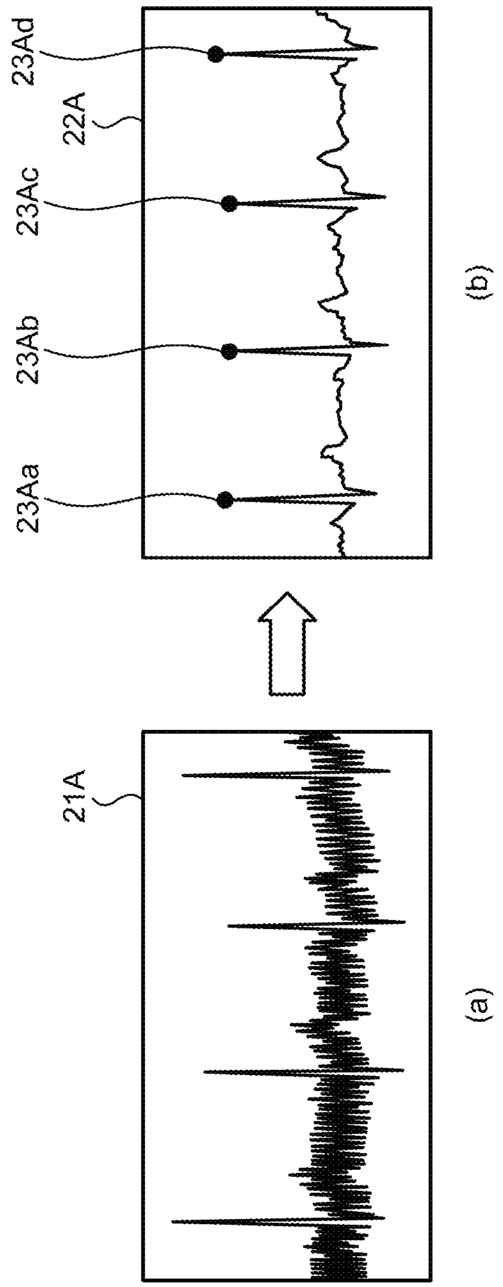
FIG. 10A is a diagram (part 1) illustrating a processing example of a wave height ratio generating unit.
Figure 10B:
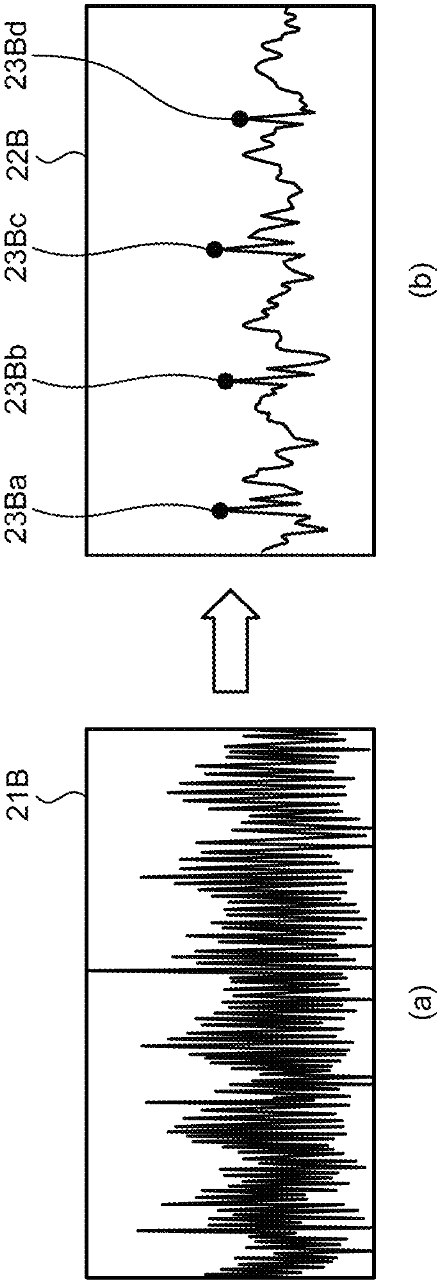
FIG. 10B is a diagram (part 2) illustrating a processing example of the wave height ratio generating unit.

FIGS. 10A and 10B are diagrams illustrating a processing example of the wave height ratio generating unit. In the filter processing according to the second embodiment, first, the input unit 31 acquires the electrocardiographic information 10 obtained from a subject 1 via an electrocardiographic signal measuring instrument 2. Waveform data 21A and 21B acquired at this point is waveform data included in the electrocardiographic information 10 and obtained by plotting with the horizontal axis as time and the vertical axis as the voltage (see (a) of FIG. 10A and (a) of FIG. 10B). At this point, the amount of noise to be superimposed is different between the waveform data 21A and the waveform data 21B, and more noise is superimposed on the waveform data 21B than on the waveform data 21A.

Next, filter processing is executed by the filter processing unit 32 to generate filtered electrocardiographic information (waveform data) 22A and 22B (see (b) of FIG. 10A and (b) of FIG. 10B). At this point, the filter processing to be executed is different between the waveform data 22A and the waveform data 22B, and since the amount of noise superimposed is large in the waveform data 21B, filter processing for smoothing is executed more on the waveform data 22B than on the waveform data 22A.

In this manner, since the influence of noise can be reduced when the filter processing is executed, extraction of the unit waveform data 13 by the unit waveform data extracting unit 33, the loss detection by the loss detection unit 34, and others, which are subsequent processing, can be performed with higher accuracy. However, in a case where the filter processing for further smoothing is executed as in the waveform data 22B, there is a concern about deformation of the waveform and reduction of the wave height.

Unit waveform data 23Aa to 23Ad and 23Ba to 23Bd included in the waveform data 22A and 22B are each associated with a wave height. Incidentally, the wave height is a wave height calculated by the unit waveform data extracting unit 33 or a wave height reset by the data interpolation unit 35.

The associated wave heights are used as a criterion for the determination of arrhythmia; however, it can be seen that the wave height is smaller in the waveform data 22B on which the filter processing for further smoothing has been executed than in the waveform data 22A. Therefore, in consideration of the determination of arrhythmia, which is the final application, if the wave height is output as it is as in the first embodiment, the filter design has to be limited in order to suppress the influence of the filter design.

Therefore, the wave height ratio generating unit 39 aggregates the wave heights associated with the unit waveform data 13 included in the waveform data 12 and generates the wave height ratio that is a relative amount. In FIGS. 10A and 10B, the average value is used as the reference (100%); however, the maximum value or the minimum value may be used as the reference.

According to this, the wave heights associated with the unit waveform data 23Aa to 23Ad and 23Ba to 23Bd can be treated as a wave height ratio in percentage rather than a voltage value in volts, and it is possible to determine the arrhythmia (detect an abnormal wave height) as usual after canceling the influence of the filter design.

According to the second embodiment described above, since the influence of the filter design can be canceled and the filter processing for further smoothing can be executed, the extraction of the unit waveform data 13 by the unit waveform data extracting unit 33, the loss detection by the loss detection unit 34, and others, which are subsequent processing, can be performed with higher accuracy.

In addition, since a waveform having a relatively large or small wave height can be found from the wave height ratio, the determination of arrhythmia, which is the final application, can be performed as usual.

Other Embodiments

Although the embodiments for carrying out the present invention have been described above, the present invention should not be limited only by the above-described embodiments. For example, it has been described that the electrocardiographic signal analysis systems 3 and 3A are provided separately from the electrocardiographic signal measuring instrument 2; however, the electrocardiographic signal analysis systems 3 and 3A may be configured integrally with the electrocardiographic signal measuring instrument 2. In addition, at least some of the functions of the electrocardiographic signal analysis systems 3 and 3A may be included in an electrocardiograph 100. For example, the electrocardiograph 100 may include the input unit 31, the filter processing unit 32, the unit waveform data extracting unit 33, the loss detection unit 34, the data interpolation unit 35, the output unit 36, and the control unit 37.

INDUSTRIAL APPLICABILITY

Using the electrocardiographic signal analysis system according to the present invention makes it possible to optimize the waveform when a peak loss occurs in an electrocardiographic waveform.

REFERENCE SIGNS LIST

1 SUBJECT
2 ELECTROCARDIOGRAPHIC SIGNAL MEASURING INSTRUMENT
3, 3A ELECTROCARDIOGRAPHIC SIGNAL ANALYSIS SYSTEM
10 ELECTROCARDIOGRAPHIC INFORMATION
11, 11A to 11C, 12, 12A to 12C, 21A, 21B, 22A, 22B WAVEFORM DATA
13, 13A to 13C, 23Aa to 23Ad, 23Ba to 23Bd UNIT WAVEFORM DATA
14, 14A to 14C INTERPOLATION DATA
31 INPUT UNIT
32 FILTER PROCESSING UNIT
33 UNIT WAVEFORM DATA EXTRACTING UNIT
34 LOSS DETECTION UNIT
35 DATA INTERPOLATION UNIT
36 OUTPUT UNIT
37 CONTROL UNIT
38 STORAGE UNIT
39 WAVE HEIGHT RATIO GENERATING UNIT
100 ELECTROCARDIOGRAM
$R_L$ LOSS PORTION

The invention claimed is:

1. An electrocardiogramal analysis system that acquires electrocardiogramformation and performs processing, the electrocardiogramanal analysis system comprising:

a processor, the processor being configured to:

receive input of the electrocardiogramformation;

perform segmentation and extract unit waveform data based on a peak of an R wave or an S wave from waveform data included in the electrocardiogramformation;

detect a loss portion of the peak of the R wave or the S wave in the unit waveform data using an extreme value immediately before or immediately after the peak or using a point of inflection immediately before or immediately after the peak, the loss portion of the peak being associated with a measurement failure of an instrument used to measure the electrocardiogramformation or an external disturbance during measurement of the electrocardiogramformation; and set a wave height or a cycle of a waveform after interpolation based on a peak position of an R wave or an S wave of a waveform obtained by interpolating the loss portion of the peak in order to suppress an erroneous determination due to an influence of the loss portion of the peak.

2. The electrocardiogramal analysis system according to claim 1, wherein concerning the unit waveform data, the processor is configured to determine whether or not a minimum point immediately before or immediately after the peak of the R wave exceeds a reference or whether or not a maximum point immediately before or immediately after the peak of the S wave is below a reference to detect the peak loss.

3. The electrocardiogramal analysis system according to claim 1, wherein concerning the unit waveform data, the processor is configured to determine whether or not a maximum point immediately before or immediately after the peak of the R wave exceeds a reference or whether or not a minimum point immediately before or immediately after the peak of the S wave is below a reference to detect the peak loss.

4. The electrocardiogramal analysis system according to claim 1, wherein concerning the unit waveform data, the processor is configured to determine whether or not the point of inflection immediately before or immediately after the peak of the R wave exceeds a reference or whether or not the point of inflection immediately before or immediately after the peak of the S wave is below a reference to detect the peak loss.

5. The electrocardiogramaignal analysis system according to claim 1, wherein the processor is further configured to:

apply a filter to the acquired electrocardiogramformation to pass the characteristic frequency and output filtered electrocardiogramformation, and extract the unit waveform data based on the filtered electrocardiogra information.

6. The electrocardiogramanal analysis system according to claim 1, wherein the processor is further configured to:

apply a filter to the acquired electrocardiogramformation to retain the frequency components of both or either the R wave and the S wave, and output filtered electrocardiogramformation, and extract the unit waveform data based on the filtered electrocardiographic information, wherein when any one of an average value, a maximum value, or a minimum value of wave heights in the unit waveform data is used as a reference, the set wave height is a relative amount concerning the reference.

7. The electrocardiogramal analysis system according to claim 1, wherein the processor is configured to generate interpolation data in which the peak loss portion is interpolated.

8. An electrocardiogramal analysis system according to comprising:

an electrocardiogram configured to measure an electrocardiogramal of a subject; and a storage; and a processor is configured to:

acquire the electrocardiogramal from the electrocardiograma the electrocardiogramformation;

extract, from waveform data included in the electrocardiogramformation, unit waveform data segmented based on a peak of an R wave or an S wave, and store the extracted unit waveform data in the storage;

detect, in the unit waveform data stored in the storage, a loss portion of the peak of the R wave or the S wave using an extreme value immediately before or immediately after the peak or using a point of inflection immediately before or immediately after the peak, the loss portion of the peak being associated with a measurement failure of the electrocardiograph or an external disturbance during measurement of the electrocardiogramformation;

interpolate the detected loss portion to generate an interpolated waveform;

set a wave height or a cycle of the interpolated waveform based on a peak position of the R wave or the S wave of the interpolated waveform so as to suppress an erroneous determination of normal sinus rhythm or arrhythmia due to an influence of the loss portion of the peak; and output the set wave height or the set cycle of the interpolated waveform to use for determining normal sinus rhythm or arrhythmia.

9. The electrocardiogramaignal analysis system according to claim 1, wherein the processor is further configured to:

control a display to display a determination of normal sinus rhythm or arrythmia based on the set wave height or the set cycle of the waveform after the interpolation based on the loss portion.

* * * * *